(12) United States Patent
Ishimaru

(10) Patent No.: US 9,474,476 B2
(45) Date of Patent: Oct. 25, 2016

(54) SPECTRAL CHARACTERISTICS MEASUREMENT DEVICE AND SPECTRAL CHARACTERISTICS MEASUREMENT METHOD

(71) Applicant: NATIONAL UNIVERSITY CORPORATION KAGAWA UNIVERSITY, Takamatsu-shi, Kagawa (JP)

(72) Inventor: Ichiro Ishimaru, Takamatsu (JP)

(73) Assignee: NATIONAL UNIVERSITY CORPORATION KAGAWA UNIVERSITY, Takamatsu-shi (JP)

( * ) Notice: Subject to any disclaimer, the term of this patent is extended or adjusted under 35 U.S.C. 154(b) by 33 days.

(21) Appl. No.: 14/380,643

(22) PCT Filed: Feb. 27, 2013

(86) PCT No.: PCT/JP2013/055228
§ 371 (c)(1),
(2) Date: Aug. 22, 2014

(87) PCT Pub. No.: WO2013/129519
PCT Pub. Date: Sep. 6, 2013

(65) Prior Publication Data
US 2015/0043001 A1 Feb. 12, 2015

(30) Foreign Application Priority Data
Feb. 29, 2012 (JP) ................. 2012-044272

(51) Int. Cl.
*G01J 3/02* (2006.01)
*A61B 5/1455* (2006.01)
(Continued)

(52) U.S. Cl.
CPC ......... *A61B 5/1455* (2013.01); *A61B 5/14532* (2013.01); *G01B 9/0207* (2013.01);
(Continued)

(58) Field of Classification Search
CPC ............ G01J 3/00; G01J 3/02; G01J 3/2823; G01B 9/02007; G01B 9/02062; G01B 9/0207

USPC .......................................................... 356/456
See application file for complete search history.

(56) References Cited

U.S. PATENT DOCUMENTS 5,943,133 A * 8/1999 Zeylikovich ........... G01B 11/00
356/496
2001/0046054 A1 11/2001 Zeylikovich et al.
(Continued)

FOREIGN PATENT DOCUMENTS

DE 697 33 430 T2 7/2006
ES 2 244 016 T3 12/2005
(Continued)

OTHER PUBLICATIONS

Aug. 18, 2015 Chinese Office Action issued in Chinese Patent Application No. 201380011702.3.
(Continued)

*Primary Examiner* — Jonathan Hansen
(74) *Attorney, Agent, or Firm* — Oliff PLC

(57) ABSTRACT

The present invention causes measurement light, emitted from an object and to be measured, to enter a fixed mirror and a movable mirror forming interfering light between the measurement light reflected by the fixed mirror and measurement light reflected by the movable mirror. Change to the intensity of the interference light of measurement light is obtained by moving the movable mirror unit, acquiring the interferogram of measurement light. Reference light of a narrow wavelength band included in a wavelength band of the measurement light enters the fixed mirror and the movable mirror, forming interference light of the reference light. The movable mirror is moved to correct the interferogram of measurement light, which is at the same wavelength as the reference light in the measurement light, and the reference light, and a spectrum of the measurement light is acquired based on the corrected interferogram.

8 Claims, 7 Drawing Sheets

(51) Int. Cl.
*G01N 21/45* (2006.01)
*G01N 21/49* (2006.01)
*A61B 5/145* (2006.01)
*G01J 3/453* (2006.01)
*G01B 9/02* (2006.01)
*G01N 21/25* (2006.01)
*G01N 21/95* (2006.01)
*G01J 3/10* (2006.01)
*G01J 3/18* (2006.01)
*A61B 5/00* (2006.01)
*G01N 21/359* (2014.01)

(52) U.S. Cl.
CPC ....... *G01B9/02041* (2013.01); *G01B 9/02049* (2013.01); *G01J 3/0205* (2013.01); *G01J 3/0229* (2013.01); *G01J 3/0256* (2013.01); *G01J 3/0272* (2013.01); *G01J 3/10* (2013.01); *G01J 3/18* (2013.01); *G01J 3/4532* (2013.01); *G01J 3/4535* (2013.01); *G01N 21/255* (2013.01); *G01N 21/45* (2013.01); *G01N 21/49* (2013.01); *G01N 21/9501* (2013.01); *A61B 5/6887* (2013.01); *A61B 5/7257* (2013.01); *A61B 2562/0233* (2013.01); *G01J 2003/102* (2013.01); *G01J 2003/4538* (2013.01); *G01N 21/359* (2013.01); *G01N 2201/0612* (2013.01)

(56) References Cited

U.S. PATENT DOCUMENTS

2002/0196450 A1* 12/2002 Olszak ............... G01B 11/2441
356/511
2003/0090674 A1    5/2003 Zeylikovich et al.
2003/0227631 A1* 12/2003 Rollins ............... G01B 9/02045
356/479

FOREIGN PATENT DOCUMENTS

| JP | A-2002-514301 | 5/2002 |
| JP | A-2002-286410 | 10/2002 |
| JP | A-2008-309706 | 12/2008 |
| JP | A-2008-309707 | 12/2008 |
| WO | WO 98/25105 A1 | 6/1998 |
| WO | 2012/004586 A1 | 1/2012 |

OTHER PUBLICATIONS

Daisuke et al., "Spectroscopic tomography of biological tissues with the near-infrared radiation for the non-invasive measurement of the biogenic-substances," Optical Diagnostics and Sensing XII: Toward Point-of-Care Diagnostics; and Design and performance Validation of Phantoms Used in Conjuction with Optical Measurement of Tissue IV, SPIEE, vol. 8229, pp. 1-7, 2012.
Dec. 18, 2014 Extended European Search Report issued in European Application No. 13754598.4.
Jan. 20, 2016 Office Action issued in Korean Patent Application No. 10-2014-7023627.
Mar. 2, 2016 Office Action issued in Canadian Patent Application No. 2,866,019.
International Search Report issued in International Application No. PCT/JP2013/055228 dated Apr. 2, 2013.
Written Opinion of the International Searching Authority issued in International Application No. PCT/JP2013/055228 dated Apr. 2, 2013.

* cited by examiner

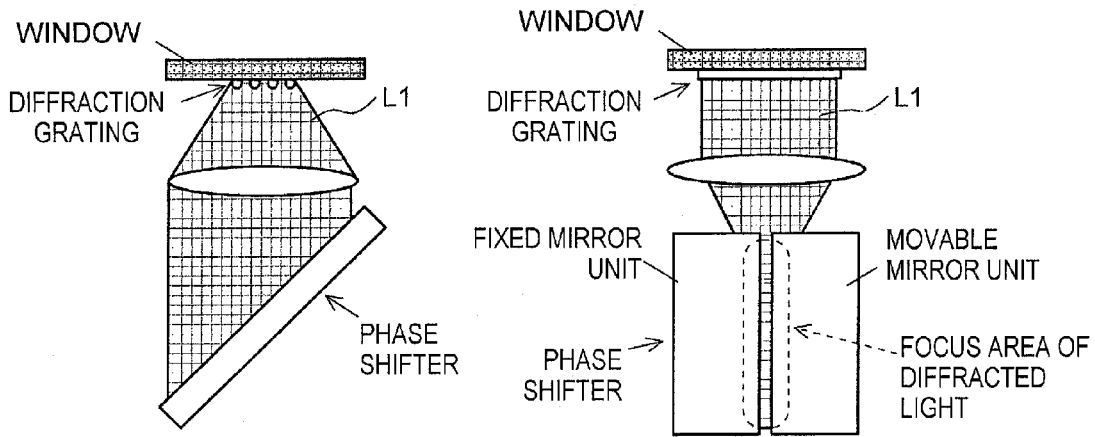
Fig. 5A FRONT VIEW  Fig. 5B SIDE VIEW
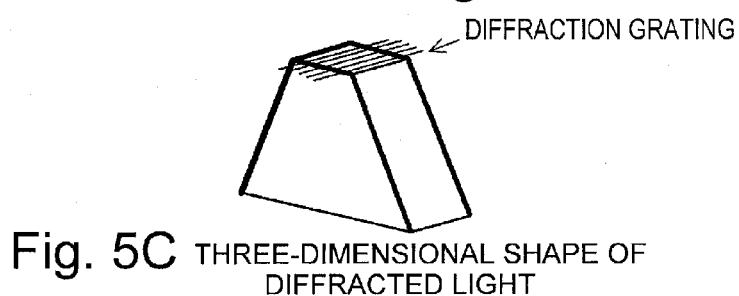
Fig. 5C THREE-DIMENSIONAL SHAPE OF DIFFRACTED LIGHT
Fig. 6
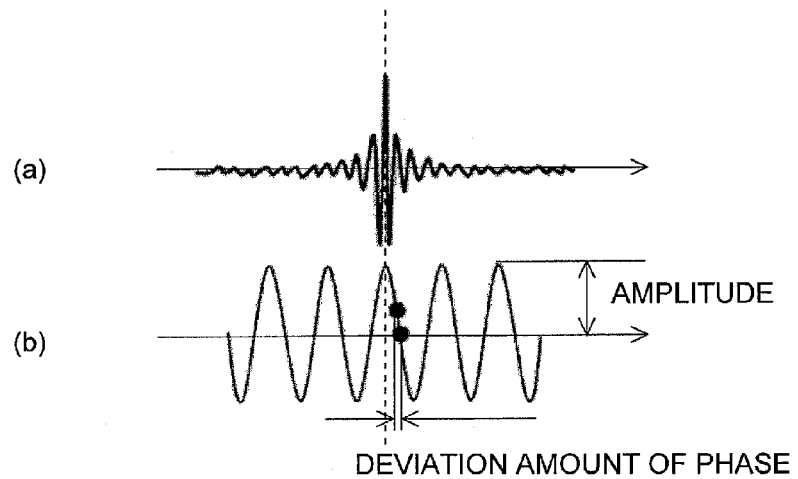

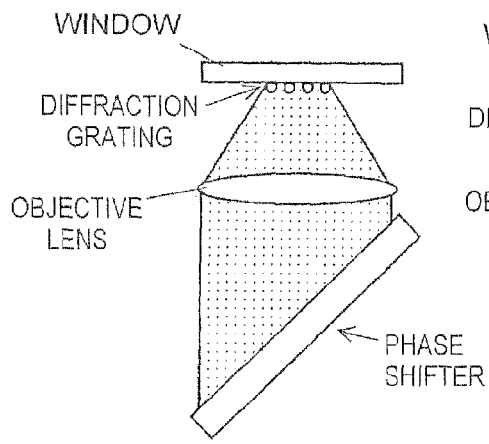 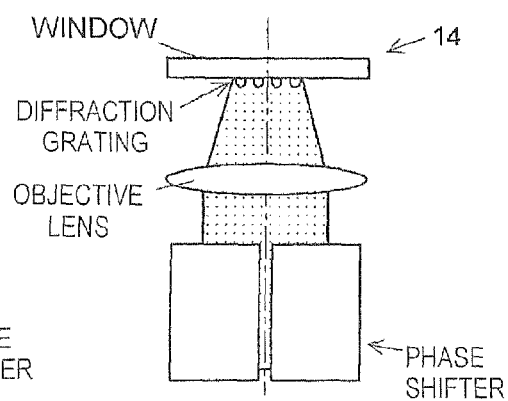
Fig. 10A  FRONT VIEW
Fig. 10B  SIDE VIEW
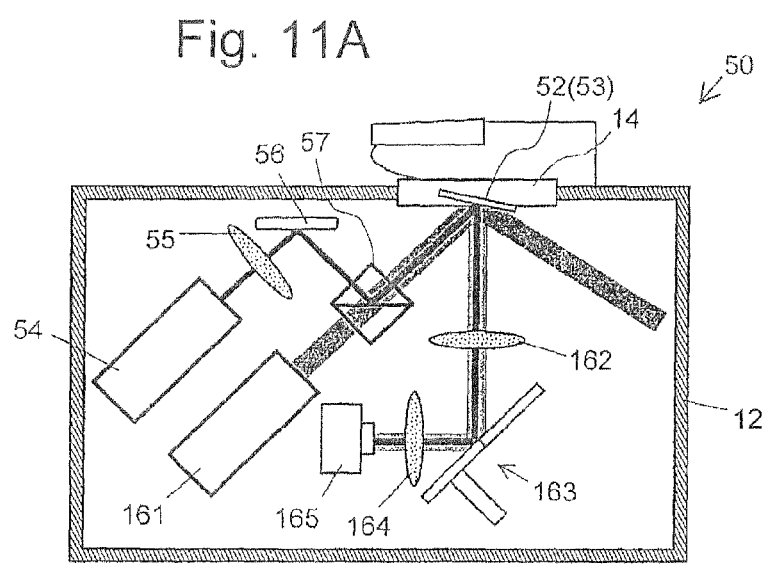
Fig. 11A
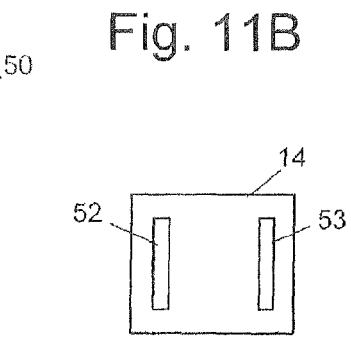
Fig. 11B

SPECTRAL CHARACTERISTICS MEASUREMENT DEVICE AND SPECTRAL CHARACTERISTICS MEASUREMENT METHOD

TECHNICAL FIELD

The present invention relates to a spectral characteristics measurement device and a spectral characteristics measurement method that can non-invasively measure biological components inside a body, such as blood sugar and blood cholesterol, and that can be used for defect assessment of a semiconductor.

BACKGROUND ART

In various diseases, such as diabetes and hyperlipidemia, management of biological components in blood, such as blood glucose (blood sugar) and blood cholesterol, is important to prevent and treat the diseases. However, to measure biological components in blood, a small amount of blood usually needs to be drawn, which is painful. And troublesome operations, such as sterilization of a blood drawing area and proper treatment of consumables, are necessary, so that, frequent blood drawing for the measurement of biological components for preventive purposes, for example, is apt to be averted.

Consequently, non-invasive measurement devices that measure biological components without drawing blood are proposed. As an example of the devices, Patent Literature 1 describes a method, wherein light is cast to a biological tested area, and as a result, biological components are detected using spectral characteristics of light (object light) emitted from biological components in the tested area.

In the method described in Patent Literature 1, an interference using an object beam generated from each bright point that optically forms the biological components is used to acquire an interferogram of the biological components, and the interferogram is Fourier-transformed to obtain spectral characteristics (spectrum) of the object light. Specifically, object light, including transmitted light and diffused/scattered light, generated from each bright point is introduced through an objective lens to a phase shifter composed of a fixed mirror unit and a movable mirror unit, and object beams reflected from the two mirror units interfere with each other on an imaging plane. The movable mirror unit is moved by a piezo element or the like, and a phase shift according to the moving distance of the movable mirror unit is given to the object beams reflected from the fixed mirror unit and the movable mirror unit. Accordingly, the intensity of the interference light is changed, and a so-called interferogram is acquired. The interferogram is Fourier-transformed to obtain the spectral characteristics (spectrum) of the object light.

CITATION LIST

Patent Literature

[Patent Literature 1] JP 2008-309707 A

SUMMARY OF INVENTION

Technical Problem

To prevent or treat diseases, it is effective to measure the concentration of biological components, such as blood sugar (glucose) and cholesterol, included in blood. For the prevention, the concentration value of such a biological component of an individual in relation to an average concentration value of a population of people of interest is significant, and for the treatment, continuous measurement of the change in the concentration value of a patient is effective. In either case, the difference and the change are minute, and the concentration value needs to be highly accurately measured.

The concentration value of the biological components, such as blood sugar (glucose) and cholesterol in blood, can be detected by casting light to a blood vessel and measuring the intensity of light at one or a plurality of specific wavelengths absorbed or reflected by object biological components in the light transmitted through or reflected by the blood vessel. However, in the conventional method, the intensity of the measurement light may be disturbed by, for example, a change in the emission strength of the light source, a change in the ambient environment including temperature and humidity, and an error in the movement of the movable mirror unit, and there is a problem that the concentration of the object biological components cannot be highly accurately measured.

Such a problem also occurs in the detection of a minute defect of a semiconductor substrate from spectral characteristics of light emitted from a semiconductor substrate when light is cast to the semiconductor substrate.

The problem to be solved by the present invention is to provide a spectral characteristics measurement device and a spectral characteristics measurement method that can highly accurately measure spectral characteristics of an object to be measured by suppressing influence of disturbance.

Solution to Problem

To solve the aforementioned problems, the present invention provides a spectral characteristics measurement device including:

a) a fixed reflection unit and a movable reflection unit;

b) an incident optical system that causes measurement light emitted from an object to be measured to enter the fixed reflection unit and the movable reflection unit;

c) an imaging optical system that forms interference light of light reflected by the fixed reflection unit and light reflected by the movable reflection unit;

d) a measurement light detection unit that detects an intensity of the interference light of measurement light formed by the imaging optical system;

e) a processing unit that acquires an interferogram of measurement light based on a change in the intensity of the interference light of measurement light obtained by moving the movable reflection unit;

f) reference light incident means for causing reference light of a narrow wavelength band included in a wavelength band of the measurement light to enter the fixed reflection unit and the movable reflection unit;

g) a reference light detection unit that detects an intensity of interference light of the reference light formed by the imaging optical system; and h) an arithmetic processing unit that corrects the interferogram of measurement light based on an amplitude of a change in the intensity of the interference light of reference light detected by the reference light detection unit by moving the movable reflection unit and based on a phase difference between narrow wavelength band measurement light having the same wavelength as the reference light in the measurement light and the reference light, and that acquires a spectrum of the measurement light based on the corrected interferogram of measurement light.

The "light of a narrow wavelength band" denotes light in a wavelength range of ±30 nm, or narrower, around the peak wavelength, and a single-wavelength laser beam emitted from a semiconductor laser light source (laser diode) is included in the light of a narrow wavelength band.

In the spectral characteristics measurement device with the previously described configuration,
the reference light incident means may be composed of: a light source; and a reflective diffraction grating that causes first-order diffracted light of light emitted from the light source to enter the incident optical system as the reference light.

Furthermore, the spectral characteristics measurement device may preferably be configured to include a plate-like window made of a light transmission member, wherein one of the surfaces is a placement surface on which the object to be measured is placed, and the other is a light casting surface, wherein
the diffraction grating is arranged on an area of part of the light casting surface, and
the light source casts light to the entire light casting surface at an angle that does not cause a specular reflected light of the light cast onto the light casting surface to enter the incident optical system.

According to the configuration, light cast to an area on the light casting surface of the window except the diffraction grating passes through the window and reaches the object to be measured. As a result, measurement light, such as scattered light and fluorescence, is emitted from the object to be measured, and the measurement light passes through the window and reaches the incident optical system. As for the light cast to the diffraction grating on the light casting surface of the window, first-order diffracted light at an emission angle determined by the wavelength and the incident angle of the light, the spacing of the diffraction grating, and other factors enters the incident optical system as the reference light. Therefore, a light source is commonly used for generating the measurement light and the reference light, and the device can be compact.

According to the configuration, the specular reflected light (0th-order light) of the light from the light source cast onto the light casting surface of the window does not enter the incident optical system, but the first-order diffracted light instead enters the incident optical system as the reference light. Though the intensity of the first-order diffracted light is much smaller than that of the specular reflected light, the intensity of light emitted from a target component is also very small. Therefore, the intensities of the measurement light and the reference light are balanced.

In the spectral characteristics measurement device with the previously described configuration,
the reference light incident means may be composed of: a light source that emits light of a narrow wavelength band included in the wavelength band of the measurement light; and a reflection film that reflects the light emitted from the light source to cause the light to enter the incident optical system.

The present invention provides a spectral characteristics measurement method including the steps of:
a) causing measurement light emitted from an object to be measured to enter a fixed reflection unit and a movable reflection unit;
b) forming interference light of light reflected by the fixed reflection unit and light reflected by the movable reflection unit;

c) acquiring an interferogram of measurement light based on a change in the intensity of the interference light of measurement light obtained by moving the movable reflection unit;
d) causing reference light of a narrow wavelength band included in a wavelength band of the measurement light to enter the fixed reflection unit and the movable reflection unit;
e) detecting an intensity of interference light of reference light reflected by the fixed reflection unit and reference light reflected by the movable reflection unit; and
f) correcting the interferogram of measurement light based on an amplitude of a change in the intensity of the interference light of reference light obtained by moving the movable reflection unit and based on a phase difference between narrow wavelength band measurement light having the same wavelength as the reference light in the measurement light and the reference light, and acquiring a spectrum of the measurement light based on the corrected interferogram of measurement light.

In the biological component measurement method, first-order diffracted light generated by a diffraction grating by casting light from a light source to the diffraction grating may be caused to enter the incident optical system as the reference light.

In the biological component measurement method, a diffraction grating can be made on an area of part of a light casting surface of a plate-like window made of a light transmission member, wherein one of the surfaces is a placement surface on which the object to be measured is placed, and the other surface is the light casting surface, wherein
the light source casts light to the entire light casting surface at an angle that does not cause the specular reflected light of the light cast onto the light casting surface to enter the incident optical system.

In the spectral characteristics measurement method with the above described configuration, light of a narrow wavelength band included in the wavelength band of the measurement light may be cast from the light source to a reflection film, and light reflected by the reflection film may be caused to enter the incident optical system as the reference light.

Advantageous Effects of the Invention

The present invention divides measurement light, such as scattered light and fluorescence emitted from an object to be measured, into two lights, gives a phase difference between the two measurement lights, causes the two measurement lights interfere with each other to acquire an interferogram of measurement light, and Fourier-transforms the interferogram to obtain a measurement light spectrum (spectral characteristics). For example, to measure a blood sugar level, spectral characteristics of scattered light generated by casting light to blood sugar (glucose) are detected to non-invasively measure the blood sugar level in the blood. In this case, the scattered light emitted from the blood sugar is very weak, so that even a small disturbance, such as an error in the movement of a movable reflection unit and a fluctuation in the intensity of light source, may change the spectral characteristics of the blood sugar. In the present invention, an incident optical system causes reference light, together with the measurement light, to enter the fixed reflection unit and the movable reflection unit, and the reflection units divide the reference light into two reflected lights to form interference light. Based on the amplitude of the change in the intensity of the interference light and the phase difference, the interferogram of measurement light is corrected. Therefore, the spectral characteristics of the measurement light can be accurately detected.

BRIEF DESCRIPTION OF THE DRAWINGS

FIG. 5A and FIG. 5B are a front view and a side view showing the first-order diffracted light from the diffraction grating, and FIG. 5C is a view three-dimensionally showing the first-order diffracted light.

FIG. 6 is a view showing a relationship between (a) the interferogram of measurement light and (b) a change in the intensity of interference light of the first-order diffracted light.

FIG. 10A and FIG. 10B are a front view and a side view showing the first-order diffracted light from the diffraction grating.

FIG. 11A and FIG. 11B are schematic views showing an overall configuration of a blood sugar level sensor according to a third embodiment of the present invention.

DESCRIPTION OF EMBODIMENTS

Hereinafter, specific embodiments applying the present invention to a blood sugar level sensor will be described with reference to the drawings.

First Embodiment

Figure 1B:
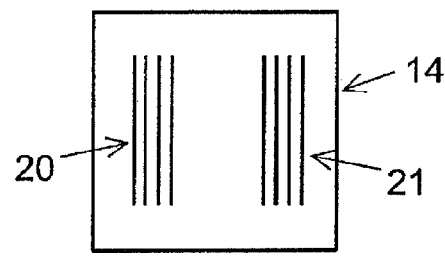
FIG. 1A and FIG. 1B are schematic views showing an overall configuration of a blood sugar level sensor according to a first embodiment of the present invention.
Figure 1A:
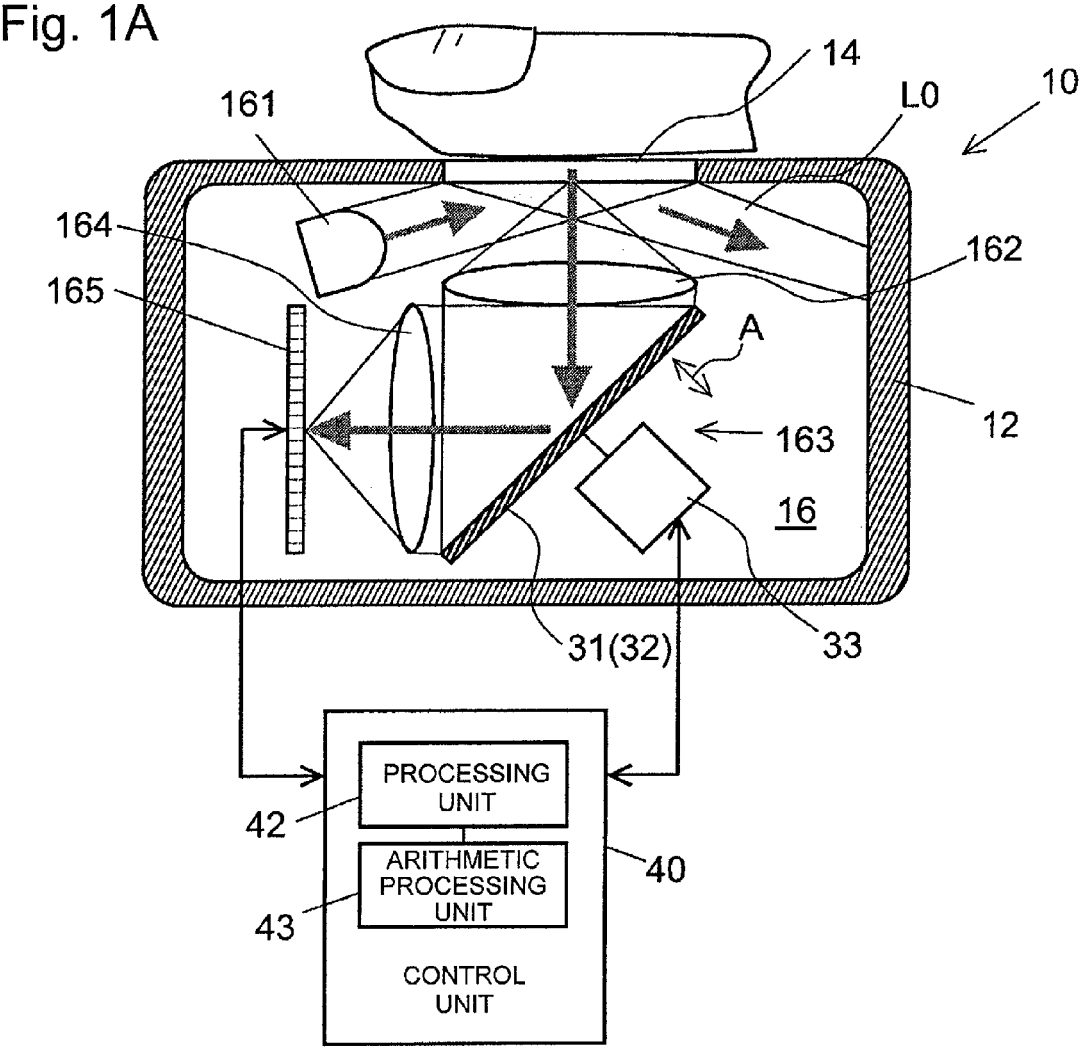

FIG. 1A and FIG. 1B show an overall configuration of a blood sugar level sensor 10 according to the present embodiment. The blood sugar level sensor 10 includes: a rectangular box-like casing 12; a rectangular plate-like window 14 fixed to one of the peripheral side surfaces of the casing 12, such as an upper surface; and a spectroscopic measurement unit 16 housed in the casing 12.

The casing 12 is made of a material that does not transmit light, such as plastic and metal. The window 14 is made of light transmissive material, and as described later, an object to be measured, such as a fingertip, is placed on the upper surface. Therefore, the upper surface of the window 14 is a placement surface. Meanwhile, diffraction gratings are formed on part of a light casting surface that is a lower surface of the window 14 positioned in the casing 12. In this embodiment, two diffraction gratings 20 and 21 extending along two opposing sides of the window 14 are formed. In the following description, areas provided with the two diffraction gratings 20 and 21 in the light casting surface of the window 14 will also be called reference light areas, and the other areas in the light casting surface of the window 14 will also be called measurement light areas. The diffraction gratings 20 and 21 are constructed by a plurality of projection lines parallel to the two sides. In the present embodiment, the interval between the projection lines is set to 1.1 µm.

The spectroscopic measurement unit 16 includes a light source 161, an objective lens 162, a phase shifter 163, an imaging lens 164, and a detection unit 165. In the present embodiment, the objective lens 162 and the imaging lens 164 are equivalent to an incident optical system and an imaging optical system, respectively. The objective lens 162 is arranged to face the light casting surface of the window 14. The imaging lens 164 is arranged such that the optical axis is orthogonal to the objective lens 162.

A light source with good permeability to the skin that emits near-infrared light at a wavelength of around 1 µm is used as the light source 161. The light source 161 is arranged in a direction such that a specular reflected light does not enter the objective lens 162 when the emission light is cast to the light casting surface of the window 14 and such that first-order diffracted light generated when the light is cast to the diffraction gratings 20 and 21 enters the objective lens 162. The first-order diffracted light from the diffraction gratings 20 and 21 is used as reference light, and therefore, the light source 161 and the diffraction gratings 20 and 21 form reference light incident means in the present embodiment.

The detection unit 165 is composed of, for example, a two-dimensional CCD (Charge Coupled Device) camera of 16×16 pixels, and the detection unit 165 is arranged such that a light-receiving surface 165a of the detection unit 165 is positioned on the imaging plane of the imaging lens 164.

Figure 2:
FIG. 2 is a view showing a light-receiving surface of a detection unit.

FIG. 2 is a view schematically showing the light-receiving surface 165a of the detection unit 165. For the convenience, the number of pixels is 10×10 in the description here. As shown in FIG. 2, many pixels are arranged on the light-receiving surface 165a of the detection unit 165, and the first-order diffracted light (reference light) generated by the diffraction grating 20 and the diffraction grating 21 is focused on top 20 (2×10) pixels and bottom 20 pixels, respectively. Therefore, the pixels serve as a reference light detection unit. The reference light detection unit may include 16 pixels excluding two pixels positioned on each of the left and right sides of the top and the bottom, excluding four pixels in total. The measurement light is focused on the pixels of the light-receiving surface 165a excluding the reference light detection units. Therefore, these pixels serve as a measurement light detection unit of the present invention. Actually, the measurement light is focused on the pixels positioned at the part indicated by an image F of a fingertip placed on the placement surface of the window 14.

As will be described in detail later, a detection signal of the detection unit 165 is input to a processing unit 42. The processing unit 42 acquires an interferogram from the detection signal from the detection unit 165. An arithmetic processing unit 43 mathematically Fourier-transforms the interferogram, and as a result, spectral characteristics (spectrum) as relative intensity at each wavelength of measurement light are obtained.

The phase shifter 163 is arranged between the objective lens 162 and the imaging lens 164. The phase shifter 163 includes a fixed mirror unit 31, a movable mirror unit 32, and a drive mechanism 33 that moves the movable mirror unit 32. The fixed mirror unit 31 and the movable mirror unit 32 are equivalent to a fixed reflection unit and a movable reflection unit of the present invention, respectively. Each of the fixed mirror unit 31 and the movable mirror unit 32 has a rectangular reflection surface inclined at an angle of 45° relative to the optical axis of the objective lens 162 and the optical axis of the imaging lens 164. The reflection surfaces of the mirror units are aligned at an very small gap.

The drive mechanism 33 includes, for example, a piezo element including a capacitance sensor. The drive mechanism 33 receives a signal from the control unit 40 and moves the movable mirror unit 32 in an arrow A direction while maintaining the inclination angle of the reflection surface relative to the optical axis at 45°. According to the configuration, the position of the movable mirror unit 32 relative to the fixed mirror unit 31 is changed, and a phase difference is provided between the light reflected by the fixed minor unit 31 and the light reflected by the movable mirror unit 32.

Specifically, the moving distance of the objective lens 162 or the imaging lens 164 of the movable mirror unit 32 in the optical axis direction is $1/\sqrt{2}$ of the moving distance of the movable mirror unit 32 in the arrow A direction. The optical path length difference that provides relative phase change between the fixed light and the movable light is twice the moving distance of the movable mirror unit 32 in the optical axis direction.

Next, an operation of using the blood sugar level sensor 10 with the previously described configuration to measure the blood sugar (glucose) in the blood of a fingertip of a test subject will be described.

The fingertip of the test subject is placed on the placement surface of the window 14. Here, the fingertip is not only placed on the placement surface of the window 14, but the fingertip is also firmly pressed against the placement surface. In this way, the fingertip can be firmly pressed against the placement surface to maintain the focal position of the objective lens 162 at a predetermined position (depth) inside of the fingertip during the measurement. The fingertip may not always be firmly pressed against the placement surface, and for example, the fingertip may be gently put on the placement surface to detect components in a blood vessel in an area near the surface of the fingertip.

In the state that the fingertip is pressed against the placement surface of the window 14, the near-infrared light from the light source 161 is cast to the light casting surface of the window 14. Consequently, the near-infrared light cast to the measurement light area of the window 14 passes through the window 14 and reaches the fingertip. The near-infrared light transmits through the skin of the fingertip and is scattered by various biological components inside of the fingertip. The light scattered by the biological components again passes through the skin of the fingertip and reaches inside of the casing 12 from the window 14. The light enters the objective lens 162.

The scattered light as measurement light emitted from the inside of the fingertip reaches the objective lens 162 while spreading in various directions, become parallel beams, and reach the entire surfaces of the fixed mirror unit 31 and the movable mirror unit 32 of the phase shifter 163. More specifically, part of the scattered light is reflected by the reflection surface of the fixed mirror unit 31, and the rest of the scattered light is reflected by the reflection surface of the movable mirror unit 32. Both of the scattered lights enter the imaging lens 164, respectively. In the following description, the scattered light reflected by the fixed mirror unit 31 will also be called a fixed scattered light, and the scattered light reflected by the movable mirror unit 32 will also be called a movable scattered light.

Figure 3:
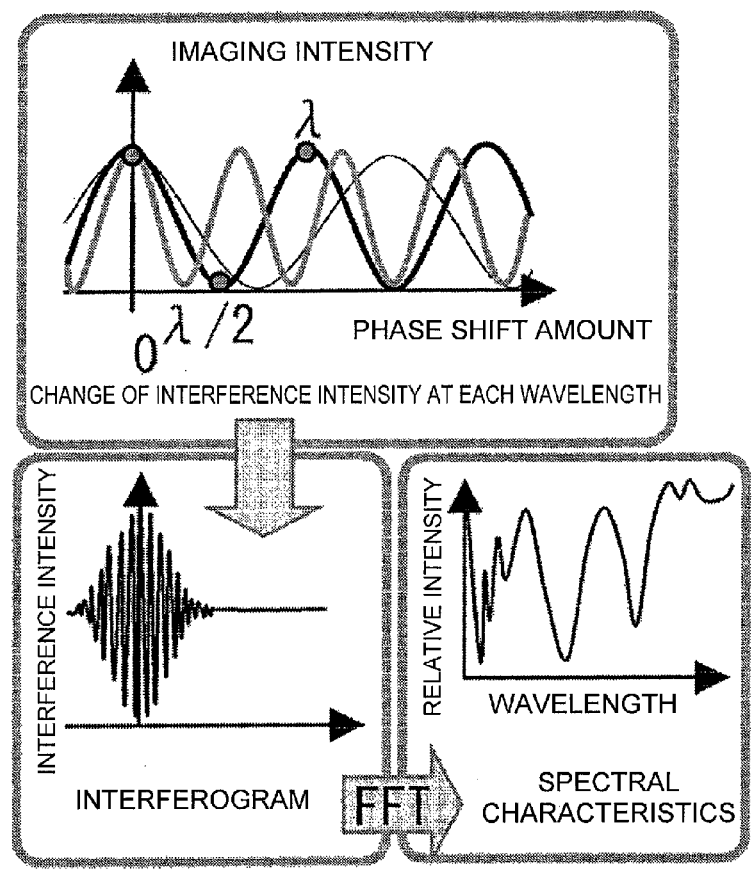
FIG. 3 is an explanatory view of a change in the intensity of interference light, and an interferogram and spectral characteristics of the interference light.

The fixed scattered light beam and the movable scattered light beam entering the imaging lens 164 are focused on the light-receiving surface 165a of the detection unit 165, and an interference image is formed. In this case, the scattered light emitted from the inside of the fingertip includes light at various wavelengths. Therefore, the movable mirror unit 32 can be moved to change the optical path length difference between the movable scattered light beam and the fixed scattered light beam to obtain a waveform of a change in the intensity of the image (a change in the intensity of interference light) called an interferogram. The interferogram can be mathematically Fourier-transformed to obtain spectral characteristics. FIG. 3 shows (a) the change in the intensity of the light at each wavelength, (b) the interferogram, and (c) the spectral characteristics.

In the blood sugar level sensor 10 of the present embodiment, only the scattered light emitted from the focal plane of the objective lens 162 positioned at a specific depth inside of the fingertip is focused on the light-receiving surface 165a of the detection unit 165, and the light generated from other part than the focal planes is not focused on the light-receiving surface 165a of the detection unit 165. Therefore, spectral characteristics inside of the fingertip, in which the depth is limited only to the focal plane, can be obtained.

Meanwhile, the near-infrared light cast to the reference light area of the window 14 is reflected by the diffraction gratings 20 and 21. In the present embodiment, the specular reflected light (light indicated by reference sign "L0" in FIG. 1A) of the light cast from the light source 161 to the light casting surface of the window 14 does not enter the objective lens 162. On the other hand, the first-order diffracted light at a specific wavelength λ determined by the numerical aperture of the objective lens 162, the spacing of the grating (interval between the projection lines) of the diffraction gratings 20 and 21, an incident angle θin, and an emission angle θout enters the objective lens 162.

Figure 4:
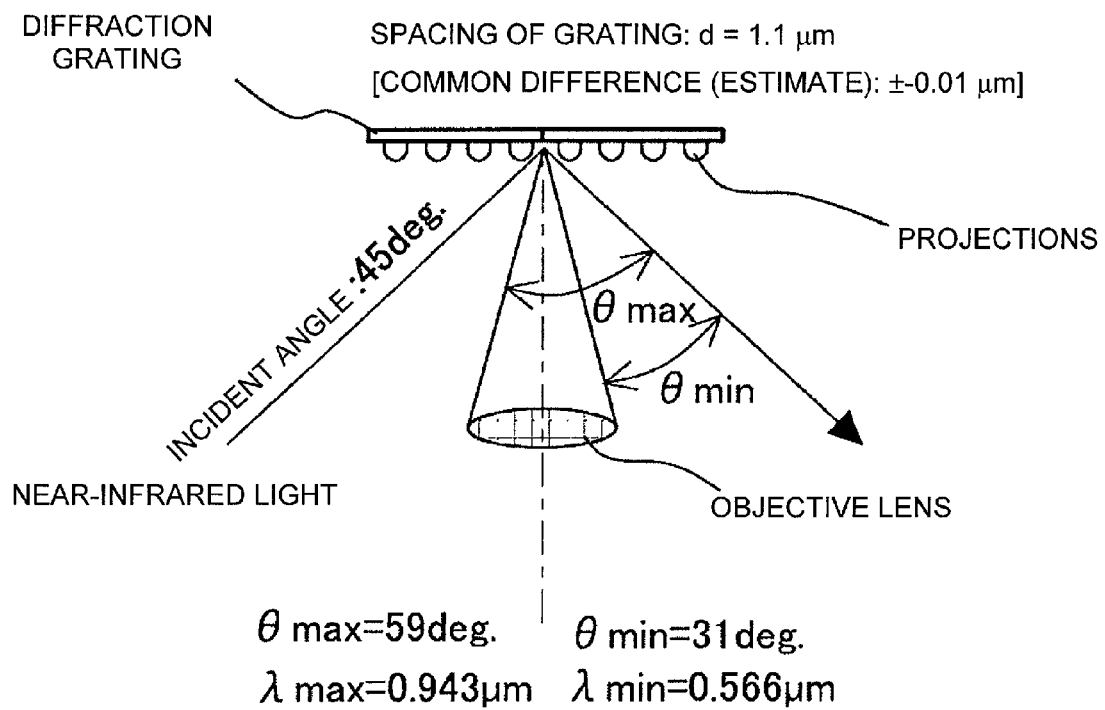
FIG. 4 is an explanatory view of a wavelength and a diffraction angle of first-order diffracted light entering an objective lens from a diffraction grating.

In the present embodiment, as shown in FIG. 4, the near-infrared light from the light source 161 is configured to enter at an incident angle 45 degree relative to the diffraction grating with the spacing of the grating (interval between the projection lines) d=1.1 μm. The objective lens 162 with a numerical aperture N.A.=0.24 (angular aperture=14 degree), a focal distance=20 mm, and a lens aperture g=ϕ10 mm is used. In this case, a minimum diffraction angle θmin on the short wavelength side entering the objective lens 162 is 31 degree, and a wavelength λmin is 0.566 μm. A maximum diffraction angle θmax on the long wavelength side is 59 degree, and a wavelength λmax is 0.943 μm. In the present embodiment, an InGaAs camera with a detected wavelength region of 0.9 μm to 1.7 μm is used as the detection unit 165. Therefore, of the first-order diffracted light entering the objective lens 162, the wavelength region detected by the detection unit 165 is an very narrow wavelength region (0.9 μm to 0.943 μm).

As shown in FIG. 5A, FIG. 5B, and FIG. 5C, the first-order diffracted light from the diffraction gratings 20 and 21 spreads in the width direction of the diffraction gratings 20 and 21 and reaches the objective lens 162 (see the front view of FIG. 5A). Parallel beams reach the objective lens 162 in the extending direction of the diffraction gratings 20 and 21 (see the side view of FIG. 5B). Therefore, the first-order diffracted light in a square pyramid shape as shown in FIG. 5C reaches the objective lens 162. As a result, the first-order diffracted light entering the objective lens 162 forms band-shaped light with a width equivalent to the width of light emitted from the light source 161 and reaches near the boundary of the fixed mirror unit 31 and the movable mirror unit 32. Part of the light is reflected by the reflection surface of the fixed mirror unit 31, and the rest of the light is reflected by the reflection surface of the movable mirror unit 32 and enters the imaging lens 164. In the following description, the first-order diffracted light reflected by the fixed mirror unit 31 will also be called fixed diffracted light, and the first-order diffracted light reflected by the movable mirror unit 32 will also be called movable diffracted light.

The fixed diffracted light and the movable diffracted light entering the imaging lens 164 are focused on the light-receiving surface 165a of the detection unit 165, and an interference image is formed. At this time, the movable mirror unit 32 can be moved to change the optical path length difference between the fixed diffracted light and the movable diffracted light to obtain a change in the intensity of the interference light. As described, the wavelength regions of the fixed diffracted light and the movable diffracted light are very narrow, and it can be stated that the lights are substantially single-wavelength lights. Therefore, the shape of the change in the intensity of the interference light obtained here is a simple cosine wave.

The light cast to the fingertip through the window 14 and the light for generating the first-order diffracted light in the diffraction gratings 20 and 21 are emitted from the same light source. Therefore, when there is a fluctuation in the light intensity emitted from the light source 161, both of the change in the intensity of the interference light of the measurement light (scattered light) and the change in the intensity of the interference light of the first-order diffracted light are affected by the fluctuation. The optical path of the measurement light and the optical path of the first-order diffracted light from the window 14 to the detection unit 165 are common. Therefore, when there is a disturbance on the common optical path, both of the change in the intensity of the interference light of measurement light and the change in the intensity of the interference light of the first-order diffracted light are affected by the disturbance.

Consequently, the arithmetic processing unit 43 of the present embodiment corrects the interferogram of measurement light based on the amplitude of the change in the intensity of the interference light of the first-order diffracted light and the phase difference between the first-order diffracted light and the measurement light at the same wavelength as the first-order diffracted light, and Fourier-transforms the corrected interferogram to acquire spectral characteristics. For example, assuming that the interferogram of measurement light as shown in FIG. 6(*a*) and the change in the intensity of the interference light of the diffracted light as shown in FIG. 6(*b*) are obtained, the interferogram is corrected by correcting the interference light intensity of the interferogram of measurement light by using the ratio of the first-order diffracted light relative to the amplitude of the change in the intensity of the interference light. The phase of the interferogram of measurement light is shifted by the deviation amount of the phase between the first-order diffracted light and the measurement light to correct the interferogram. As a result, the influence of the fluctuation in the light intensity of the light source 161 and the disturbance generated on the optical path can be suppressed, and the interferogram of measurement light can be accurately acquired.

Figure 7:
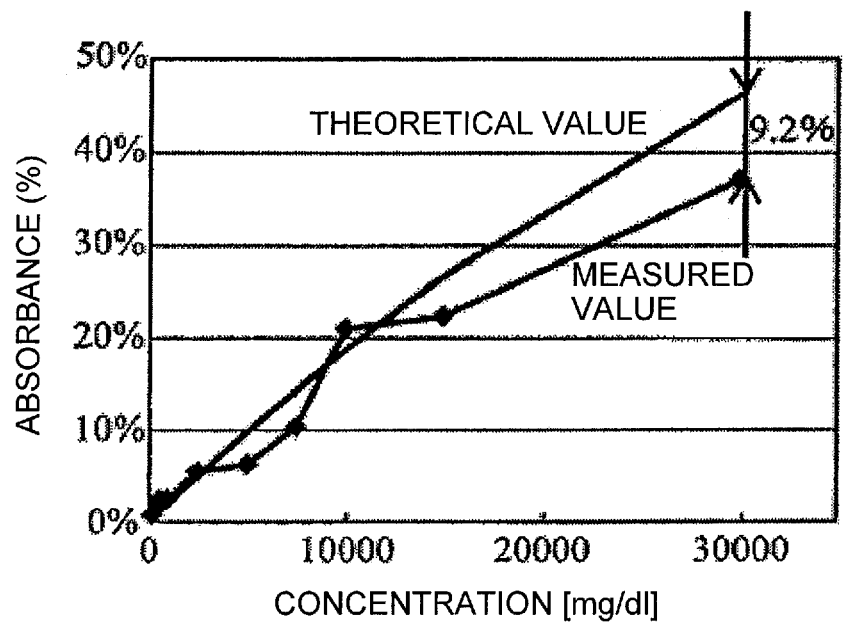
FIG. 7 is a view showing measurement results.

FIG. 7 shows a result of measurement of the glucose concentration in a test tube using the blood sugar level sensor 10 of the present embodiment. As shown in FIG. 7, although the values do not completely coincide with theoretical values, the absorbance tends to be high depending on the concentration, and an excellent correlation between the glucose concentration and the absorbance is obtained. Although the glucose concentration in general human blood is about 100 mg/dl, and it is recognized that the glucose concentration can be detected with such a low concentration.

Second Embodiment

Figure 8A:
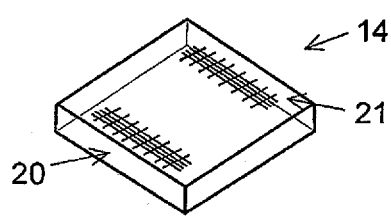
FIG. 8A and FIG. 8B are a perspective view and a top view showing a window used in the blood sugar level sensor according to a second embodiment of the present invention.
Figure 8B:
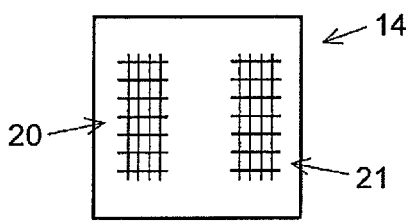

FIG. 8A and FIG. 8B show a configuration of the window 14 used in the blood sugar level sensor 10 according to a second embodiment of the present invention. The second embodiment is different from the first embodiment in that the diffraction gratings 20 and 21 arranged on the light casting surface of the window 14 include first projection lines parallel to one side of the window 14 and second projection lines orthogonal to the projection lines.

In the present embodiment, a interval (spacing of the grating) between the first projection lines is the same as those of the diffraction grating of the first embodiment while, an interval (diffraction period) of the second projection lines is d=3.9 μm. The numerical aperture of the objective lens 162, the focal distance, the lens aperture and the incident direction of the near-infrared light from the light source 161 relative to the light casting surface are the same as those of the first embodiment. Therefore, the same first-order diffracted light as that of the first embodiment is generated from the first projection lines.

Figure 9:
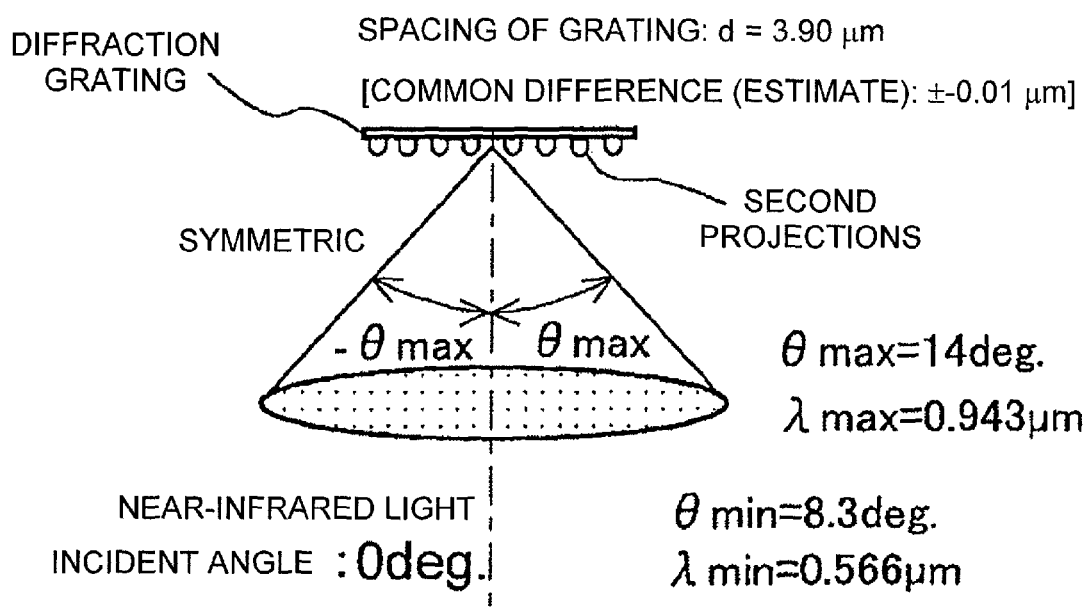
FIG. 9 is an explanatory view of a wavelength and a diffraction angle of first-order diffracted light entering the objective lens from second projection lines of the diffraction grating.

On the other hand, since the second projection lines and the incident direction of the near-infrared light are parallel to each other, the near-infrared light is entered at an incident angle of 0 degree. relative to the second projection lines as shown in FIG. 9. Therefore, first-order diffracted light that is symmetric across the incident light is emitted at the second projection lines of the diffraction gratings 20 and 21. Specifically, the minimum diffraction angle θmin on the short wavelength side of the light entering the objective lens 162 is ±8.3 degree, and the wavelength λmin of the first-order diffracted light is 0.566 μm. The maximum diffraction angle θmax on the long wavelength side is ±14 degree, and the wavelength λmax of the first-order diffracted light is 0.943 μm. Therefore, the wavelength range detected by the detection unit 165 including the InGaAs camera with the detection wavelength region of 0.9 μm to 1.7 μm is also 0.9 μm to 0.943 μm for the first-order diffracted light at the second projection lines.

According to the configuration, the first-order diffracted light from the diffraction gratings 20 and 21 spreads in the extending directions of both of the first projection lines and the second projection lines of the diffraction gratings 20 and 21 and reaches the objective lens 162 in the present embodiment as shown in FIG. 10A and FIG. 10B. As a result, as for the first-order diffracted light entering the objective lens 162, light wider than that of the blood sugar level sensor 10 of the first embodiment reaches the boundary of the fixed mirror unit 31 and the movable mirror unit 32. Therefore, the first-order diffracted light can be easily divided into two. Furthermore, compared to the first embodiment, the light intensity of the first-order diffracted light can be stronger.

The closer the light intensity of the first-order diffracted light used as the reference light to the light intensity of the measurement light (scattered light) emitted from the object to be measured is, the more accurate the correction of the interferogram of measurement light is. Therefore, the sizes of the formation areas of the diffraction gratings 20 and 21 and whether to form the diffraction gratings by one set of projection lines or two sets of projection lines can be appropriately determined according to the light intensity of the measurement light.

Third Embodiment

FIG. 11A and FIG. 11B show a blood sugar level sensor 50 according to a third embodiment of the present invention. The third embodiment is different from the first embodiment in that a laser beam, instead of the first-order diffracted light, is used as the reference light. Specifically, in place of the diffraction gratings, reflection films 52 and 53 are arranged on the light casting surface of the window 14 in the blood sugar level sensor 50. A laser beam source 54 is arranged in the casing 12 alongside a light source 161, and light from the laser beam source 54 enters the reflection film 52 arranged in the window 14 through a lens 55, a mirror 56, and a beam splitter 57. The laser beam source 54 emits a narrow-wavelength band laser beam (single-wavelength laser beam) of part of the wavelength band of the light emitted from the light source 161.

The single-wavelength laser beam from the laser beam source 54 entering the reflection film 52 is reflected by the reflection film 52 to enter the objective lens 162 and is used as the reference light.

The near-infrared light from the light source 161 enters the reflection film 53 and areas of the light casting surface of the window 14 excluding the reflection films 52 and 53. The near-infrared light from the light source 161 entering the areas of the light casting surface excluding the reflection films 52 and 53 reaches the fingertip through the window 14 and is scattered by various biological components inside of the fingertip. The scattered light as measurement light passes through the skin of the fingertip to reach inside of the casing 12 from the window 14 and enters the objective lens 162. Meanwhile, the near-infrared light from the light source 161 entering the reflection film 53 is reflected by the reflection film 53, enters the objective lens 162 and is used as the reference light. Since the light entering the objective lens 162 from the reflection film 53 is a specular reflected light, the intensity is much greater than the scattered light from the inside of the fingertip. Therefore, a dark filter (not shown) is attached to the reflection film 53 to keep a balance with the intensity of the scattered light, and a reflected light with weak intensity enters the objective lens 162. The laser beam emitted from the laser beam source 54 is also set to weak intensity according to the scattered light.

In the previously described configuration, each of the laser beam reflected by the reflection film 52 and entering the objective lens 162 and the near-infrared light reflected by the reflection film 53 and entering the objective lens 162 is divided into two lights by the phase shifter 163, and the light enters the imaging lens 164. The laser beam entering the imaging lens 164 is focused at substantially one point on the light-receiving surface 165a of the detection unit 165 and interfered. On the other hand, the near-infrared light entering the imaging lens 164 is focused on the light-receiving surface 165a of the detection unit 165, and an interference image is formed.

At this time, the movable mirror unit 32 can be moved to obtain a change in the intensity of the interference light of each of the laser beam as the reference light and the near-infrared light. Since the laser beam is single-wavelength, the change in the intensity of the interference light is a simple cosine wave as in the first-order diffracted light described in the first embodiment. The optical path of the measurement light (scattered light) and the optical path of the laser beam from the window 14 to the detection unit 165 are common. Therefore, when there is a disturbance on the common optical path, both of the change in the intensity of the interference lights of the measurement light and that of the laser beam are affected by the disturbance. Therefore, the interferogram of measurement light is corrected based on the amplitude of the change in the intensity of the interference light of the laser beam and the phase difference of the measurement light of the laser beam in the present embodiment. As a result, the influence of the disturbance on the optical path can be suppressed.

On the other hand, like the measurement light (scattered light), the reflected light of the near-infrared light from the reflection film 53 is multi-wavelength, and the change in the intensity of the interference light serves as the interferogram. The measurement light and the reflected light from the reflection film 53 are affected by the fluctuation of the light intensity of the light source 161. The measurement light and the reflected light from the reflection film 53 share the optical path from the window 14 to the detection unit 165. Therefore, when a disturbance is generated on the common optical path, both of the measurement light and the reflected light from the reflection film 53 are affected by the disturbance. Therefore, the phase and the intensity of the interferogram of the reflected light are used to correct the phase and the intensity of the interferogram of the scattered light in the present embodiment. As a result, the influence of the disturbance on the optical path and the influence of the fluctuation of the light of the light source 161 can be suppressed.

In this way, both of the light from the light source 161 and the light from the laser beam source 54 are used as the reference light in the present embodiment, and the interferogram of measurement light can be further accurately acquired.

The present invention is not limited to the embodiments, and changes can be appropriately made. For example, a drive mechanism that can moves the objective lens in the optical axis direction may be arranged. According to the configuration, the focal position of the objective lens, that is, the depth of the measurement point inside of the object to be measured, can be changed.

The present invention can also be applied to a device that detects the presence or absence of a minute defect, a foreign matter, or the like on a substrate, such as a semiconductor, based on spectral characteristics of a reflected light (measurement light) emitted from the substrate when light is cast to the substrate.

The fixed mirror unit and the movable mirror unit can be reflection plates, such as stainless plates whose surfaces are mirror-polished and glass substrates whose surfaces are coated with metal films made of aluminium or the like.

The present invention can also be applied to a Fourier-transform infrared spectrophotometer (FT-IR) that uses a Michelson interferometer to measure an interferogram to acquire a spectrum (spectral characteristics) by Fourier-transforming the interferogram.

Although one reference light is used to correct the interferogram in the above embodiments, a plurality of reference lights may be used.

REFERENCE SINGS LIST 10, 50 . . . Blood Sugar Level Sensors
12 . . . Casing
14 . . . Window
16 . . . Spectroscopic Measurement Unit 161 . . . Light Source
162 . . . Objective Lens
163 . . . Phase Shifter
164 . . . Imaging Lens
165 . . . Detection Unit
165a . . . Light-Receiving Surface
20, 21 . . . Diffraction Gratings
31 . . . Fixed Mirror Unit
32 . . . Movable Mirror Unit
33 . . . Drive Mechanism
40 . . . Control Unit
42 . . . Processing Unit
43 . . . Arithmetic Processing Unit
52, 53 . . . Reflection Film

The invention claimed is:

1. A spectral characteristics measurement device comprising:
 a fixed mirror and a movable mirror;
 an incident optical system that causes measurement light emitted from an object to be measured to enter the fixed mirror and the movable mirror, wherein the fixed mirror and movable mirror are positioned adjacent to each other in an area such that: (1) the measurement light reaches the area defined by the fixed mirror and the movable mirror and (2) a part of the measurement light is reflected by the fixed mirror and a different part of the measurement light is reflected by the movable mirror;
 an imaging optical system that forms interference light of the light reflected by the fixed mirror and the light reflected by the movable mirror;
 a measurement light detector that detects an intensity of the interference light of measurement light formed by the imaging optical system, wherein
 an interferogram of measurement light is acquired based on a change in the intensity of the interference light of measurement light obtained by moving the movable mirror;
 a light casting surface that causes reference light of a narrow wavelength band included in a wavelength band of the measurement light to enter the fixed mirror and the moveable mirror; and
 a reference light detector that detects an intensity of interference light of the reference light formed by the imaging optical system, wherein
 the interferogram of measurement light is corrected based on an amplitude of a change in the intensity of the interference light of the reference light detected by the reference light detector by moving the movable mirror and based on a phase difference between narrow wavelength band measurement light having the same wavelength as the reference light in the measurement light and the reference light, and that acquires a spectrum of the measurement light based on the corrected interferogram of measurement light.

2. The spectral characteristics measurement device according to claim 1, wherein the reference light incident means comprises:
 a light source; and
 a reflective diffraction grating that causes first-order diffracted light of light emitted from the light source to enter the incident optical system as the reference light.

3. The spectral characteristics measurement device according to claim 2, further comprising
 a plate-like window made of a light transmission member, wherein one of the surfaces is a placement surface on which the object to be measured is placed, and the other is a light casting surface, wherein
 the diffraction grating is arranged on an area of part of the light casting surface, and
 the light source is configured to cast light to the entire light casting surface at an angle that does not cause a specular reflected light of the light cast onto the light casting surface to enter the incident optical system.

4. The spectral characteristics measurement device according to claim 1, wherein
 the reference light incident means comprises:
 a light source that emits light of a narrow wavelength band included in the wavelength band of the measurement light; and
 a reflection film that reflects the light emitted from the light source to cause the light to enter the incident optical system.

5. A spectral characteristics measurement method comprising steps of:
 a) causing measurement light emitted from an object to be measured to enter a fixed mirror and a movable mirror, wherein the fixed mirror and movable mirror are positioned adjacent to each other in an area such that:(1) the measurement light reaches the area defined by the fixed mirror and the movable mirror and (2) a part of the measurement light is reflected by the fixed mirror and a different part of the measurement light is reflected by the movable mirror;
 b) forming interference light of the light reflected by the fixed mirror and the light reflected by the movable mirror;
 c) acquiring an interferogram of measurement light based on a change in the intensity of the interference light of measurement light obtained by moving the movable mirror;
 d) causing reference light of a narrow wavelength band included in a wavelength band of the measurement light to enter the fixed mirror and the movable mirror;
 e) detecting an intensity of interference light of reference light reflected by the fixed mirror and reference light reflected by the movable mirror; and
 f) correcting the interferogram of measurement light based on an amplitude of a change in the intensity of the interference light of the reference light obtained by moving the movable mirror and based on a phase difference between narrow wavelength band measurement light having the same wavelength as the reference light in the measurement light and the reference light, and acquiring a spectrum of the measurement light based on the corrected interferogram of measurement light.

6. The spectral characteristics measurement method according to claim 5, wherein
 first-order diffracted light generated by a diffraction grating by casting light from a light source to the diffraction grating is caused to enter the incident optical system as the reference light.

7. The spectral characteristics measurement method according to claim 6, wherein
 the diffraction grating is made on an area of part of a light casting surface of a plate-like window made of a light transmission member, wherein one of the surfaces is a placement surface on which the object to be measured is placed, and the other surface is the light casting surface, wherein
 the light source casts light to the entire light casting surface at an angle that does not cause the specular reflected light of the light is cast onto the light casting surface to enter the incident optical system.

8. The spectral characteristics measurement method according to claim 5, wherein
light of a narrow wavelength band included in the wavelength band of the measurement light is cast from the light source to a reflection film, and light reflected by the reflection film is caused to enter the incident optical system as the reference light.

* * * * *